(12) United States Patent
Scheuing et al.

(10) Patent No.: US 8,535,729 B2
(45) Date of Patent: Sep. 17, 2013

(54) NATURAL SILVER DISINFECTANT COMPOSITIONS

(75) Inventors: David R. Scheuing, Danville, CA (US); Erika Szekeres, San Ramon, CA (US); Steven Bromberg, Livermore, CA (US)

(73) Assignee: The Clorox Company, Oakland, CA (US)

( * ) Notice: Subject to any disclaimer, the term of this patent is extended or adjusted under 35 U.S.C. 154(b) by 880 days.

(21) Appl. No.: 12/329,400

(22) Filed: Dec. 5, 2008

(65) Prior Publication Data

US 2010/0143494 A1 Jun. 10, 2010

(51) Int. Cl.
*A01N 59/16* (2006.01)
*A01N 55/02* (2006.01)
*A01N 33/04* (2006.01)
*A01N 33/08* (2006.01)
*A01P 1/00* (2006.01)

(52) U.S. Cl.
USPC .................. 424/618; 514/495; 514/727

(58) Field of Classification Search
None
See application file for complete search history.

(56) References Cited

U.S. PATENT DOCUMENTS

| | | | |
|---|---|---|---|
| 5,401,441 A | 3/1995 | Robert et al. | |
| 6,197,814 B1 | 3/2001 | Arata | |
| 6,242,009 B1 | 6/2001 | Batarseh et al. | |
| 6,630,172 B2 | 10/2003 | Batarseh et al. | |
| 6,841,527 B2 | 1/2005 | Mitra et al. | |
| 6,939,566 B2 | 9/2005 | Batarseh et al. | |
| 7,012,053 B1 | 3/2006 | Barnabas et al. | |
| 2003/0035848 A1 | 2/2003 | Batarseh et al. | |
| 2005/0202066 A1 | 9/2005 | Arata et al. | |
| 2006/0051430 A1 | 3/2006 | Arata et al. | |
| 2006/0115440 A1 | 6/2006 | Arata et al. | |
| 2006/0293201 A1 | 12/2006 | Simon et al. | |
| 2006/0293202 A1 | 12/2006 | Cate et al. | |
| 2007/0241306 A1 | 10/2007 | Wehner et al. | |

FOREIGN PATENT DOCUMENTS

| | | | |
|---|---|---|---|
| JP | 47016504 A | * | 5/1972 |
| WO | WO 00/62618 | | 10/2000 |

OTHER PUBLICATIONS

Kawakita T. L-Monosodium glutamate (MSG). Kirk-Othmer Encyclopedia of Chemical Technology. John Wiley & Sons, Inc. (published online Dec. 4, 2000).*
Kosswig, K. Surfactants. Ullmann's Ecyclopedia of Industrial Chemistry. Wiley-VCH Verlag GmbH & Co. KgaA, pp. 431, 450, 469 (published online Jun. 15, 2000; DOI: 10.1002/14356007.a25_747).*
Singh et al. Amine oxides: a review. J. Oleo Sci., vol. 55, No. 3, 99-119 (2006).*
CAS Registry No. 1643-20-5 (Nov. 16, 1984).*
International Search Report of PCT Application No. PCT/US2009/66436, Jan. 27, 2010, 2 pages.

* cited by examiner

*Primary Examiner* — Daniel Sullivan
*Assistant Examiner* — Peter Anthopolos
(74) *Attorney, Agent, or Firm* — Alok Goel; Stacy H. Combs

(57) ABSTRACT

An antimicrobial composition contains a soluble silver salt and an alkanolamine or aminoalcohol. The composition may additionally contain an amino acid or amino acid salt and surfactant. The composition has additional stability and activity compared to prior art silver complexes.

2 Claims, No Drawings

NATURAL SILVER DISINFECTANT COMPOSITIONS

BACKGROUND OF THE INVENTION

1. Field of the Invention

The present invention relates generally to antimicrobial compositions for use on hard and soft surfaces. The invention also relates to cleaning compositions for use alone or with cleaning substrates. The composition also relates to natural cleaning compositions having a limited number of ingredients and having good cleaning properties and low residue.

2. Description of the Related Art

Silver ion based antimicrobial compositions are well-known but suffer from instability because silver ions are precipitated by a variety of anions at neutral pH, which severely limits the robustness of formulations containing surfactants and/or lower quality water because trace amounts of chloride ions in surfactants or water will readily cause precipitation of silver chloride, which causes formulation haziness and possible loss of antimicrobial activity.

To overcome this instability silver dihydrogen citrate has been developed as a "complexed" form of silver ion for example in U.S. Pat. No. 6,197,814 and U.S. Pat. App. 2006/0051430 to Arata. This complex is rather "weak", and is generally restricted to low pH, for example around pH 2. To improve the antimicrobial efficacy U.S. Pat. App. 2005/0202066 to Arata adds an additional antimicrobial, such as a quaternary ammonium compound or an oxidizer to the composition. To promote greater stability at low pH, PCT App. WO 00/62618 to Batarseh et al. discloses silver ions chelated with amino acids, such as glutamic acid.

Prior art compositions do not combine effective soluble silver ion stability with rapid antimicrobial efficacy and the surface and personal safety advantages of use at higher pH levels. It is therefore an object of the present invention to provide an antimicrobial composition that overcomes the disadvantages and shortcomings associated with prior art antimicrobial compositions.

SUMMARY OF THE INVENTION

In accordance with the above objects and those that will be mentioned and will become apparent below, one aspect of the present invention comprises an antimicrobial composition comprising a soluble silver salt; and a complexing agent selected from the group consisting of an alkanolamine, an aminoalcohol, and combinations thereof; and wherein the pH is 6 or greater.

In accordance with the above objects and those that will be mentioned and will become apparent below, another aspect of the present invention comprises a cleaning composition comprising a surfactant; a soluble silver salt; and an alkanolamine.

In accordance with the above objects and those that will be mentioned and will become apparent below, another aspect of the present invention comprises antimicrobial composition comprising a soluble silver salt; a complexing agent selected from the group consisting of an alkanolamine, an aminoalcohol, and combinations thereof; and a chelant selected from the group consisting of an aminoacid, aminoacid derivative, and combinations thereof.

Further features and advantages of the present invention will become apparent to those of ordinary skill in the art in view of the detailed description of preferred embodiments below, when considered together with the attached claims.

DETAILED DESCRIPTION OF THE INVENTION

Before describing the present invention in detail, it is to be understood that this invention is not limited to particularly exemplified systems or process parameters that may, of course, vary. It is also to be understood that the terminology used herein is for the purpose of describing particular embodiments of the invention only, and is not intended to limit the scope of the invention in any manner.

All publications, patents and patent applications cited herein, whether supra or infra, are hereby incorporated by reference in their entirety to the same extent as if each individual publication, patent or patent application was specifically and individually indicated to be incorporated by reference.

It must be noted that, as used in this specification and the appended claims, the singular forms "a," "an" and "the" include plural referents unless the content clearly dictates otherwise. Thus, for example, reference to a "surfactant" includes two or more such surfactants.

The term "comprising", which is synonymous with "including," "containing," or "characterized by," is inclusive or open-ended and does not exclude additional, unrecited elements or method steps. See MPEP 2111.03. See, e.g., Mars Inc. v. H.J. Heinz Co., 377 F.3d 1369, 1376, 71 USPQ2d 1837, 1843 (Fed. Cir. 2004) ("like the term 'comprising,' the terms 'containing' and 'mixture' are open-ended."). Invitrogen Corp. v. Biocrest Mfg., L.P., 327 F.3d 1364, 1368, 66 USPQ2d 1631, 1634 (Fed. Cir. 2003) ("The transition 'comprising' in a method claim indicates that the claim is open-ended and allows for additional steps."); Genentech, Inc. v. Chiron Corp., 112 F.3d 495, 501, 42 USPQ2d 1608, 1613 (Fed. Cir. 1997) See MPEP 2111.03. ("Comprising" is a term of art used in claim language which means that the named elements are essential, but other elements may be added and still form a construct within the scope of the claim.); Moleculon Research Corp. v. CBS, Inc., 793 F.2d 1261, 229 USPQ 805 (Fed. Cir. 1986); In re Baxter, 656 F.2d 679, 686, 210 USPQ 795, 803 (CCPA 1981); Ex parte Davis, 80 USPQ 448, 450 (Bd. App. 1948). See MPEP 2111.03. The term "consisting essentially of" as used herein, limits the scope of a claim to the specified materials or steps "and those that do not materially affect the basic and novel characteristic(s)" of the claimed invention. In re Herz, 537 F.2d 549, 551-52, 190 USPQ 461, 463 (CCPA 1976) (emphasis in original).

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In the application, effective amounts are generally those amounts listed as the ranges or levels of ingredients in the descriptions, which follow hereto. Unless otherwise stated, amounts listed in percentage ("%'s") are in weight percent (based on 100% active) of the cleaning composition alone, not accounting for the substrate weight. Each of the noted cleaner composition components and substrates is discussed in detail below.

The term "antimicrobial composition" as used herein means a composition suitable for application to a surface for the purpose of reducing the number of germs on the surface.

The compositions, herein, can be effective against Gram positive bacteria, Gram negative bacteria, fungi, yeasts, molds, and viruses.

"Controlling" the growth of at least one microorganism includes maintaining a microorganism population at a desired level (including undetectable levels such as zero population), reducing a microorganism population to a desired level, and/or inhibiting or slowing the growth of at least one microorganism. Thus, materials and mediums susceptible to attack by at least one microorganism are preserved and/or protected from this attack and the resultant deleterious effects. The present invention also provides a method for controlling the growth of at least one microorganism in or on a material or medium susceptible to attack by the microorganism which comprises the step of adding to the material or medium a composition of the present invention in an amount effective to control the growth of the microorganism. Microorganisms, as used herein, include, but are not limited to bacteria, fungi, algae, viruses, amoebae, spores, and the like, and include both yeasts and molds.

The biocides described herein have a variety of applications and uses. They are suitable for the disinfection of exposed surfaces in homes, hospitals, public areas and transportation vehicles, exhaust air and ventilation systems. The compositions can also be added to swimming pools, fountains, and the like for the control of microorganisms responsible for bio-fouling. The compositions also are useful in fish, poultry and cattle farming and the like.

The term "cleaning composition", as used herein, is meant to mean and include a cleaning formulation having at least one surfactant.

The term "surfactant", as used herein, is meant to mean and include a substance or compound that reduces surface tension when dissolved in water or water solutions, or that reduces interfacial tension between two liquids, or between a liquid and a solid. The term "surfactant" thus includes anionic, nonionic and/or amphoteric agents.

Silver or Other Metal Ion

Silver salts can be directly dissolved in water or by electrolysis of silver electrodes. Silver dihydrogen citrate can be made by immersing silver electrodes in an aqueous electrolyte solution that contains citric acid. An electrolytic potential is then applied to the electrodes, whereby silver ion is generated in the solution. When combined in this way, silver ions and citric acid form silver dihydrogen citrate, which is stable in aqueous solution. In some embodiments of the invention, the electrolyte contains greater than about 5% and more particularly greater than about 10% citric acid (% wt/volume). The silver dihydrogen citrate can then be formulated or combined with other ingredients as further described herein. Other sources of soluble silver ion are also suitable, for example silver nitrate. Silver dihydrogen citrate, produced be electrolysis or otherwise, contain high levels of citrate ion that can lead to filming and streaking. For compositions where filming and streaking are important, other soluble silver salts, such as silver nitrate may be more suitable.

Alkanolamine and Aminoalcohol

Complexes of monoethanolamine (MEA) with silver ion are quite useful for preventing silver chloride formation over a wide range of pH. The source of silver ions can be silver nitrate or any other soluble silver salt. Alternatively, MEA can be used as a "complexing titrant" for silver dihydrogen citrate, in which most of the MEA is used to neutralize the citric acid that comes in with the silver ions when silver dihydrogen citrate is the source. Monoethanolamine, diethanolamine and triethanolamine have similar complex formation constants, and all can be used. Monoethanolamine also aids cleaning performance, for example bacon grease removal rates. Monoethanolamine is expected to be relatively mild to eye tissues, since it is used as a buffer in contact lens cleaning formulations. Ammonia forms even stronger complexes with silver ion, but generates strong odor. Other suitable complexing alkanolamines and amino alcohols include monopropanolamine, dipropanolamine, 2-methyl-2-aminopropanediol, 2-ethyl-2-aminopropanediol, 2-amino-2-methylpropanol, 2-dimethylamino-2-methyl-1-propanediol, 2-amino-2-ethylpropanol, 2-aminobutanol, tri(hydroxymethyl)aminomethane (TRIS), 2-dimethylamino-2-methylpropanol (DMAMP), N,N'-tetra-methyl-1,3-diamino-2-propanol, N,N-bis(2-hydroxyethyl)glycine (bicine) and N-tris(hydroxymethyl)methyl glycine (tricine).

Amino Acid

Compositions suitably contain amino acids and aminoacid salts, including glycine, or the salts of glutamic acid. The amino acids are edible, in general, and those that are derived from plant sources come from renewable sources. Monosodium glutamate is, of course, edible, and plant-derived. Suitable examples of amino acid compounds which can be used include, but are not limited to, $\alpha$-amino acids. Specific examples include, but are not limited to, isoleucine, phenylalanine, leucine, lysine, methionine, threonine, tryptophan, valine, alanine, glycine, arginine, histidine, hydroxyproline, $\alpha$-aminobutyric acid, asparagine, aspartic acid, cysteine, glutamic acid, glutamine, pherylalanine, proline, serine, tyrosine, and derivatives thereof and mixtures thereof.

Alkylpolyglucoside

The cleaning compositions contain alkylpolyglucoside surfactant. The cleaning compositions preferably have an absence of other nonionic surfactants, expecially synthetic nonionic surfactants, such as ethoxylates. The cleaning compositions preferably have an absence of other surfactants, such as anionic, cationic, and amphoteric surfactants. Suitable alkyl polyglucoside surfactants are the alkylpolysaccharides that are disclosed in U.S. Pat. No. 5,776,872 to Giret et al.; U.S. Pat. No. 5,883,059 to Furman et al.; U.S. Pat. No. 5,883,062 to Addison et al.; and U.S. Pat. No. 5,906,973 to Ouzounis et al., which are all incorporated by reference. Suitable alkyl polyglucosides for use herein are also disclosed in U.S. Pat. No. 4,565,647 to Llenado describing alkylpolyglucosides having a hydrophobic group containing from about 6 to about 30 carbon atoms, or from about 10 to about 16 carbon atoms and polysaccharide, e.g., a polyglycoside, hydrophilic group containing from about 1.3 to about 10, or from about 1.3 to about 3, or from about 1.3 to about 2.7 saccharide units. Optionally, there can be a polyalkyleneoxide chain joining the hydrophobic moiety and the polysaccharide moiety. A suitable alkyleneoxide is ethylene oxide. Typical hydrophobic groups include alkyl groups, either saturated or unsaturated, branched or unbranched containing from about 8 to about 18, or from about 10 to about 16, carbon atoms. Suitably, the alkyl group can contain up to about 3 hydroxy groups and/or the polyalkyleneoxide chain can contain up to about 10, or less than about 5, alkyleneoxide moieties. Suitable alkyl polysaccharides are octyl, nonyldecyl, undecyldodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses and/or galactoses. Suitable mixtures include coconut alkyl, di-, tri-, tetra-, and pentaglucosides and tallow alkyl tetra-, penta-, and hexaglucosides.

Suitable alkylpolyglycosides (or alkylpolyglucosides) have the formula: $R^2O(C_nH_{2n}O)_t(glucosyl)_x$ wherein $R^2$ is selected from the group consisting of alkyl, alkylphenyl, hydroxyalkyl, hydroxyalkylphenyl, and mixtures thereof in which the alkyl groups contain from about 10 to about 18, preferably from about 12 to about 14, carbon atoms; n is about 2 or about 3, preferably about 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantely the 2-position.

A group of alkyl glycoside surfactants suitable for use in the practice of this invention may be represented by formula I below:

$$RO—(R^2O)_y\text{-}(G)_xZ_b \qquad I$$

wherein R is a monovalent organic radical containing from about 6 to about 30 (preferably from about 8 to about 18) carbon atoms; $R^2$ is a divalent hydrocarbon radical containing from about 2 to about 4 carbon atoms; O is an oxygen atom; y is a number which has an average value from about 0 to about 1 and is preferably 0; G is a moiety derived from a reducing saccharide containing 5 or 6 carbon atoms; and x is a number having an average value from about 1 to 5 (preferably from 1.1 to 2); Z is $O_2M^1$, $O_2CR^3$, $O(CH_2)$, $CO_2M^1$, $OSO_3M^1$, or $O(CH_2)SO_3M^1$; $R^3$ is $(CH_2)CO_2M^1$ or $CH=CHCO_2M^1$; (with the proviso that Z can be $O_2M^1$ only if Z is in place of a primary hydroxyl group in which the primary hydroxyl-bearing carbon atom, $—CH_2OH$, is oxidized to form a $—CO_2M^1$ group); b is a number from 0 to 3x+1 preferably an average of from 0.5 to 2 per glycosal group; p is 1 to 10, $M^1$ is $H^-$ or an organic or inorganic cation, such as, for example, an alkali metal, ammonium, monoethanolamine, or calcium. As defined in Formula I, R is generally the residue of a fatty alcohol having from about 8 to 30 or 8 to 18 carbon atoms. Suitable alkylglycosides include, for example, APG 325® (a $C_9$-$C_{11}$ alkyl polyglycoside available from Cognis Corporation), APG 625® (a $C_{10}$-$C_{16}$ alkyl polyglycoside available from Cognis Corporation), Dow Triton® CG110 (a $C_8$-$C_{10}$ alkyl polyglycoside available from Dow Chemical Company), AG6202® (a $C_8$ alkyl polyglycoside available from Akzo Nobel), Glucopon® 225DK, and Alkadet 15® (a $C_8$-$C_{10}$ alkyl polyglycoside available from Huntsman Corporation). A C8 to C10 alkylpolyglucoside includes alkylpolyglucosides wherein the alkyl group is substantially C8 alkyl, substantially C10 alkyl, or a mixture of substantially C8 and C10 alkyl. Suitably, the alkyl polyglycoside is present in the cleaning composition in an amount ranging from about 0.01 to about 5 weight percent, or 0.1 to 5.0 weight percent, or 0.5 to 5 weight percent, or 0.5 to 4 weight percent, or 0.5 to 3 weight percent, or 0.5 to 2.0 weight percent, or 0.1 to 0.5 weight percent, or 0.1 to 1.0 weight percent, or 0.1 to 2.0 weight percent, or 0.1 to 3.0 weight percent, or 0.1 to 4.0 weight percent.

Other Surfactants

The compositions can contain other surfactants, with or without APG. In one embodiment of the invention the anionic surfactant is an alkyl sulfate having a $C_{12}$ or longer chain, for example sodium lauryl sulfate. Typical alkyl sulfate surfactants are water soluble salts or acids of the formula $ROSO_3M$ wherein R preferably is a $C_{10}$-$C_{24}$ hydrocarbyl, preferably an alkyl or hydroxyalkyl having a $C_{10}$-$C_{20}$ alkyl component, more preferably a $C_{12}$-$C_{18}$ alkyl or hydroxyalkyl, and M is H or a cation, e.g., an alkali metal cation (e.g. sodium, potassium, lithium), or ammonium or substituted ammonium (e.g. methyl-, dimethyl-, and trimethyl ammonium cations and quaternary ammonium cations such as tetramethyl-ammonium and dimethyl piperdinium cations and quaternary ammonium cations derived from alkylamines such as ethylamine, diethylamine, triethylamine, and mixtures thereof, and the like). Typically, alkyl chains of include $C_{12}$-$C_{16}$ alkyl and $C_{16\text{-}18}$ alkyl chains.

In another embodiment of the present invention, the anionic surfactant is an α-sulfomethyl ester (MES). In a suitable embodiment, the α-sulfomethyl ester is chosen from a $C_{12}$-$C_{18}$ sodium methyl α-sulfomethyl ester and a $C_{12}$-$C_{18}$ disodium α-sulfo fatty acid salt. Because more than one α-sulfomethyl ester may be present, the present invention contemplates the use of both sodium methyl α-sulfomethyl ester and the disodium α-sulfo fatty acid salt in the secondary surfactant system. Commercially available sodium α-sulfomethyl esters that may be used in accordance with the present invention include ALPHA-STEP® ML-40 and ALPHA-STEP® MC-48, both sold by Stepan Company. A mixture of sodium methyl 2-sulfolaurate and disodium 2-sulfolaurate is preferred.

Besides sodium salts, other salts of anionic surfactants can include, for example, potassium, ammonium, and substituted ammonium salts such as mono-, di- and triiethanolamine salts of the anionic surfactant. The anionic surfactant is typically present in 0.1 to 50%, or 0.1 to 30%, or 0.1 to 20%, or 1 to 20%, 3 to 20%, or 0.1 to 2%.

In one embodiment of the invention the cleaning compositions can contain amine oxides, amidoamine oxides, alkanol amides, and fatty acid amines surfactants. A suitable alkanolamide is a lower alkanolamide of a higher alkanoic acid, for example a mono-alkanolamide chosen from lauryl/myristic monoethanolamide and coco monoethanolamide from Stepan Company®. Suitable amine oxides include those compounds having the formula $R^3(OR^4)_xNO(R^5)2$ wherein $R^3$ is selected from an alkyl, hydroxyalkyl, acylamidopropyl and alkylphenyl group, or mixtures thereof, containing from 8 to 26 carbon atoms; $R^4$ is an alkylene or hydroxyalkylene group containing from 2 to 3 carbon atoms, or mixtures thereof-, x is from 0 to 5, preferably from 0 to 3; and each $R^5$ is an alkyl or hydroxyalkyl group containing from 1 to 3, or a polyethylene oxide group containing from 1 to 3 ethylene oxide groups. Preferred are C10-C18 alkyl dimethylamine oxide, and C10-18 acylamido alkyl dimethylamine oxide. A suitable example of an alkyl amphodicarboxylic acid is Miranol™ C2M Conc. manufactured by Miranol, Inc., Dayton, N.J.

Other suitable surfactants include mono-alkoxylated amine surfactants preferably of the general formula: $R^1R^2R^3N^+ApR^4X^-$ wherein $R^1$ is an alkyl or alkenyl moiety containing from about 6 to about 18 carbon atoms, preferably 6 to about 16 carbon atoms, most preferably from about 6 to about 14 carbon atoms; $R^2$ and $R^3$ are each independently alkyl groups containing from one to about three carbon atoms, preferably methyl, most preferably both $R^2$ and $R^3$ are methyl groups; $R^4$ is selected from hydrogen (preferred), methyl and ethyl; $X^-$ is an anion such as chloride, bromide, methylsulfate, sulfate, or the like, to provide electrical neutrality; A is a alkoxy group, especially a ethoxy, propoxy or butoxy group; and p is from 0 to about 30, preferably 2 to about 15, most preferably 2 to about 8. Preferably the $ApR^4$ group in the formula has p=1 and is a hydroxyalkyl group, having no greater than 6 carbon atoms whereby the —OH group is separated from the quaternary ammonium nitrogen atom by no more than 3 carbon atoms. Particularly preferred $ApR^4$ groups are —CH2CH2-0H, —CH2CH2CH2-0H, —CH2CH(CH3)-OH and —CH(CH3)CH2-OH, with —CH2CH2-OH being particularly preferred. Preferred $R^1$ groups are linear alkyl groups. Linear $R^1$ groups having from 8 to 14 carbon atoms are preferred.

The cleaning composition may contain one or more additional surfactants selected from anionic, cationic, ampholytic, amphoteric and zwitterionic surfactants and mixtures thereof. A typical listing of anionic, ampholytic, and zwitterionic classes, and species of these surfactants, is given in U.S. Pat. No. 3,929,678 to Laughlin and Heuring. A list of suitable cationic surfactants is given in U.S. Pat. No. 4,259,217 to Murphy. Where present, anionic, ampholytic, amphoteric and zwitterionic surfactants are generally used in combination with one or more nonionic surfactants. The surfactants may be present at a level of from about 0% to 90%, or from about 0.001% to 50%, or from about 0.01% to 25% by weight, or from about 0.1% to 2% by weight.

Solvent

The cleaning compositions can contain limited amounts of organic solvents, such as ethanol, propylene glycol, glycerol, and 1,3-propanediol, for example less than 10%, or less than 5%. In one embodiment the composition is free from substantial quantities of ethanol, propylene glycol, glycerol, and 1,3-propanediol since for suitable compositions the rate of antimicrobial efficacy is not dependent on the presence of these solvents. In one embodiment, the compositions can be free of other organic solvents (or only trace amounts of less than 0.5% or 0.1%) including, but are not limited to, other $C_{1-6}$ alkanols, other $C_{1-6}$ diols, $C_{1-10}$ alkyl ethers of alkylene glycols, $C_{3-24}$ alkylene glycol ethers, polyalkylene glycols, short chain esters, isoparafinic hydrocarbons, mineral spirits, alkylaromatics, terpenes, terpene derivatives, terpenoids, terpenoid derivatives, formaldehyde, and pyrrolidones. Alkanols include, but are not limited to, methanol, ethanol, n-propanol, isopropanol, butanol, pentanol, and hexanol, and isomers thereof. Diols include, but are not limited to, methylene, ethylene, propylene and butylene glycols. Alkylene glycol ethers include, but are not limited to, ethylene glycol monopropyl ether, ethylene glycol monobutyl ether, ethylene glycol monohexyl ether, diethylene glycol monopropyl ether, diethylene glycol monobutyl ether, diethylene glycol monohexyl ether, propylene glycol methyl ether, propylene glycol ethyl ether, propylene glycol n-propyl ether, propylene glycol monobutyl ether, propylene glycol t-butyl ether, di- or tripolypropylene glycol methyl or ethyl or propyl or butyl ether, acetate and propionate esters of glycol ethers. Short chain esters include, but are not limited to, glycol acetate, and cyclic or linear volatile methylsiloxanes. Water insoluble solvents such as isoparafinic hydrocarbons, mineral spirits, alkylaromatics, terpenoids, terpenoid derivatives, terpenes, and terpenes derivatives can be mixed with a water-soluble solvent when employed.

The compositions suitably contain the organic solvent ethanol, either absolute, various dilutions with water or denatured alcohol, for example denatured with isopropanol. Natural forms of ethanol can be derived from the fermentation of biomass or the hydrolysis of cellulose. Synthetic ethanol can be derived from the catalytic hydration of ethylene. Suitably, the solvent is present in the cleaning composition in an amount ranging from about 0.01 to about 5 weight percent, or 0.1 to 5.0 weight percent, or 0.1 to 4.0 weight percent, or 0.1 to 3.0 weight percent, or 0.1 to 2.0 weight percent, or 0.1 to 1.0 weight percent, or 0.5 to 5.0 weight percent, or 0.5 to 4.0 weight percent, or 0.5 to 3.0 weight percent, or 0.5 to 2.0 weight percent, or 0.5 to 1.0 weight percent.

Glycerol

The cleaning compositions can contain glycerol, or glycerin. The glycerol may be natural, for example from the saponification of fats in soap manufacture, or synthetic, for example by the oxidation and hydrolysis of allyl alcohol. The glycerol may be crude or highly purified. The glycerol can serve to compatibilize the alkyl polyglucoside, the ethanol and the lemon oil or d-limonene. Proper compatibilization of these components in suitable ratios, such as demonstrated in the examples below, allow these limited components to perform as well as complex formulated conventional synthetic cleaning compositions. Suitably, the glycerol is present in the cleaning composition in an amount ranging from about 0.01 to about 2 weight percent, or 0.05 to 2.0 weight percent, or 0.05 to 1.0 weight percent, or 0.05 to 0.5 weight percent, or 0.05 to 1.0 weight percent, or 0.10 to 2.0 weight percent, or 0.10 to 1.0 weight percent, or 0.11 to 0.5 weight percent.

Lemon Oil D-Limonene and Other Essential Oils

The cleaning compositions contain the natural essential oils or fragrances containing d-limonene or lemon oil or d-limonene. Lemon oil or d-limonene helps the performance characteristics of the cleaning composition to allow suitable consumer performance with natural ingredients and a minimum of ingredients. Lemon oil and d-limonene compositions which are useful in the invention include mixtures of terpene hydrocarbons obtained from the essence of oranges, e.g., cold-pressed orange terpenes and orange terpene oil phase ex fruit juice, and the mixture of terpene hydrocarbons expressed from lemons and grapefruit. The essential oils may contain minor, non-essential amounts of hydrocarbon carriers. Suitably, lemon oil, d-limonene, or essential oils containing d-limonene are present in the cleaning composition in an amount ranging from about 0.01 to about 0.50 weight percent, or 0.01 to 0.40 weight percent, or 0.01 to 0.30 weight percent, or 0.01 to 0.25 weight percent, or 0.01 to 0.20 weight percent, or 0.01 to 0.10 weight percent, or 0.05 to 0.40 weight percent, or 0.05 to 0.30 weight percent, or 0.05 to 0.25 weight percent, or 0.05 to 0.20 weight percent, or 0.05 to 0.10 weight percent.

Essential oils include, but are not limited to, those obtained from thyme, lemongrass, citrus, lemons, oranges, anise, clove, aniseed, pine, cinnamon, geranium, roses, mint, lavender, citronella, eucalyptus, peppermint, camphor, sandalwood, rosmarin, vervain, fleagrass, lemongrass, ratanhiae, cedar and mixtures thereof Preferred essential oils to be used herein are thyme oil, clove oil, cinnamon oil, geranium oil, eucalyptus oil, peppermint oil, mint oil or mixtures thereof.

Actives of essential oils to be used herein include, but are not limited to, thymol (present for example in thyme), eugenol (present for example in cinnamon and clove), menthol (present for example in mint), geraniol (present for example in geranium and rose), verbenone (present for example in vervain), eucalyptol and pinocarvone (present in eucalyptus), cedrol (present for example in cedar), anethol (present for example in anise), carvacrol, hinokitiol, berberine, ferulic acid, cinnamic acid, methyl salycilic acid, methyl salycilate, terpineol and mixtures thereof. Preferred actives of essential oils to be used herein are thymol, eugenol, verbenone, eucalyptol, terpineol, cinnamic acid, methyl salycilic acid, and/or geraniol.

Other essential oils include Anethole 20/21 natural, Aniseed oil china star, Aniseed oil globe brand, Balsam (Peru), Basil oil (India), Black pepper oil, Black pepper oleoresin 40/20, Bois de Rose (Brazil) FOB, Borneol Flakes (China), Camphor oil, Camphor powder synthetic technical, Canaga oil (Java), Cardamom oil, Cassia oil (China), Cedarwood oil (China) BP, Cinnamon bark oil, Cinnamon leaf oil, Citronella oil, Clove bud oil, Clove leaf, Coriander (Russia), Coumarin (China), Cyclamen Aldehyde, Diphenyl oxide, Ethyl vanilin, Eucalyptol, Eucalyptus oil, Eucalyptus citriodora, Fennel oil, Geranium oil, Ginger oil, Ginger oleoresin (India), White grapefruit oil, Guaiacwood oil, Gurjun balsam, Heliotropin, Isobornyl acetate, Isolongifolene, Juniper berry oil, L-methyl acetate, Lavender oil, Lemon oil, Lemongrass oil, Lime oil distilled, Litsea Cubeba oil, Longifolene, Menthol crystals, Methyl cedryl ketone, Methyl chavicol, Methyl salicylate, Musk ambrette, Musk ketone, Musk xylol, Nutmeg oil, Orange oil, Patchouli oil, Peppermint oil, Phenyl ethyl alcohol, Pimento berry oil, Pimento leaf oil, Rosalin, Sandalwood oil, Sandenol, Sage oil, Clary sage, Sassafras oil, Spearmint oil, Spike lavender, Tagetes, Tea tree oil, Vanilin, Vetyver oil (Java), and Wintergreen. Each of these botanical oils is commercially available.

Builders and Chelating Agents

The cleaning composition can include a builder, which increases the effectiveness of the surfactant. The builder can also function as a softener, a sequestering agent, a buffering agent, or a pH adjusting agent in the cleaning composition. The builder can be selected from inorganic builders, such as alkali metal carbonate, alkali metal bicarbonate, alkali metal hydroxide, alkali metal silicate and combinations thereof. These builders are often obtained from natural sources. A variety of builders or buffers can be used and they include, but are not limited to, phosphate-silicate compounds, zeolites, alkali metal, ammonium and substituted ammonium polyacetates, trialkali salts of nitrilotriacetic acid, carboxylates, polycarboxylates, carbonates, bicarbonates, polyphosphates, aminopolycarboxylates such as EDTA, polyhydroxy-sulfonates, and starch derivatives. Builders, when used, include, but are not limited to, alkali metal and alkaline earth salts of organic acids, mineral acids, silicate, metasilicate, polysilicate, borate, hydroxide, carbonate, carbamate, phosphate, polyphosphate, pyrophosphates, triphosphates, tetraphosphates, and hydroxide. Useful inorganic buffers/alkalinity sources include ammonia, the alkali metal carbonates and alkali metal phosphates, e.g., sodium carbonate, ammonium carbamate, sodium polyphosphate. For additional buffers see WO 95/07971, which is incorporated herein by reference. Other preferred pH adjusting agents include sodium or potassium hydroxide. The buffer silicate is meant to encompass silicate, metasilicate, polysilicate, aluminosilicate and similar compounds.

One aspect of the invention are salts of 2-hydroxycarboxylic acid or mixture of 2-hydroxycarboxylic acids or derivatives. Examples of 2-hydroxycarboxylic acids include tartaric acid, citric acid, malic acid, mandelic acid, glycolic acid, and lactic acid. 2-Hydroxycarboxylic acids also include polymeric forms of 2-hydroxycarboxylic acid, such as polylactic acid. Since other organic builders are not substantially present, significant amounts of 2-hydroxycarboxylic acids are required.

Suitable amino carboxylates chelating agents include ethanol-diglycines, disodium cocoyl glutamatic acid, and methyl glycine di-acetic acid (MGDA), both in their acid form, or in their alkali metal, ammonium, and substituted ammonium salt forms. Further carboxylate chelating agents for use herein include salicylic acid, aspartic acid, glutamic acid, glycine, malonic acid or mixtures and derivatives thereof.

The compositions can contain substantially no additional builders or organic chelating agents. Suitable compositions comprise builders or chelating agents in concentrations of 0.5 to 10% by weight, or 0.5 to 5% by weight, or 0.5 to 4% by weight, or 0.5 to 3% by weight, or 0.5 to 2% by weight.

Disinfectant or Sanitizer

The cleaning compositions can contain no, or substantially no, additional disinfectants or sanitizers, such as quaternary ammonium antimicrobials or biguanides. Although the compositions may contain minor amounts of traditional antimicrobials as preservatives or other uses, the compositions are without the use of traditional quaternary ammoniom compounds or phenolics. Non-limiting examples of these quaternary compounds include benzalkonium chlorides and/or substituted benzalkonium chlorides, di(C6-C14)alkyl di short chain (C1-4 alkyl and/or hydroxyalkl)quatemaryammonium salts, N-(3-chloroallyl)hexaminium chlorides, benzethonium chloride, methylbenzethonium chloride, and cetylpyridinium chloride. Other quaternary compounds include the group consisting of dialkyldimethyl ammonium chlorides, alkyl dimethylbenzylammonium chlorides, dialkylmethyl-enzylmmonium chlorides, and mixtures thereof. Biguanide antimicrobial actives including, but not limited to polyhexamethylene biguanide hydrochloride, p-chloro-henyl biguanide; 4-chlorobenzhydryl biguanide, halogenated hexidine such as, but not limited to, chlorhexidine (1,1'-hexamethylene-bis-5-(4-chlorophenyl biguanide) and its salts are also in this class. In one embodiment, the cleaning compositions can contain no, or substantially no, additional disinfectants or sanitizers, such as organic acids, quaternary ammonium antimicrobials or biguanides.

In another embodiment, antimicrobial agents, in addition to 2-hydroxy-carboxylic acids and other ingredients, include quaternary ammonium compounds and phenolics. Non-limiting examples of these quaternary compounds include benzalkonium chlorides and/or substituted benzalkonium chlorides, di($C_6$-$C_{14}$)alkyl di short chain ($C_{1-4}$ alkyl and/or hydroxyalkl)quaternary ammonium salts, N-(3-chloroallyl) hexaminium chlorides, benzethonium chloride, methylbenzethonium chloride, and cetylpyridinium chloride. Other quaternary compounds include the group consisting of dialkyldimethyl ammonium chlorides, alkyl dimethylbenzylammonium chlorides, dialkylmethyl-benzylammonium chlorides, and mixtures thereof. Biguanide antimicrobial actives including, but not limited to polyhexa-methylene biguanide hydrochloride, p-chlorophenyl biguanide; 4-chlorobenzhydryl biguanide, halogenated hexidine such as, but not limited to, chlorhexidine (1,1'-hexamethylene-bis-5-(4-chlorophenyl biguanide) and its salts are also in this class. Additional antimicrobial agents include those employed in the art for use in oral, topical and mucous membrane treating solutions and compositions in applications suitable for incidental human ingestion owing to their extremely low toxicities and low irritancy characteristics. These are sometimes denoted as "acceptable oral antimicrobials" in the art.

pH

The pH of the cleaning composition is measured directly without dilution. The cleaning compositions can have a pH of 6 or above, 7 or above, or 7.5 or above, or 8 or above, or 9 or above, or 10 or above, or from 4 to 11, or from 7.5 to 11, or from 8 to 11, or from 9 to 11.

Natural Thickener

The present compositions can also comprise an auxiliary nonionic or anionic polymeric thickening component, especially cellulose thickening polymers, especially a water-soluble or water dispersible polymeric materials, having a molecular weight greater than about 20,000. By "water-soluble or water dispersible polymer" is meant that the material will form a substantially clear solution in water at a 0.5 to 1 weight percent concentration at 25° C. and the material will increase the viscosity of the water either in the presence or absence of surfactant. Examples of water-soluble polymers which may desirably be used as an additional thickening component in the present compositions, are hydroxyethylcellulose, hydroxypropyl cellulose, hydroxypropyl methylcellulose, dextrans, for example Dextran purified crude Grade 2P, available from D&O Chemicals, carboxymethyl cellulose, plant exudates such as acacia, ghatti, and tragacanth, seaweed extracts such as sodium alginate, and sodium carrageenan. Preferred as the additional thickeners for the present compositions are natural polysaccharide or cellulose materials. Examples of such materials are guar gum, locust bean gum, and xanthan gum. Also suitable herein preferred is hydroxyethyl cellulose having a molecular weight of about 700,000. The thickeners are generally present in amounts of 0.05 to 2.0 weight percent, or 0.1 to 2.0 weight percent.

Dyes and Colorants

The cleaning compositions optionally contain dyes or colorants or contain one or more, or none of these components. These dyes, colorants and preservatives can be natural (occurring in nature or slightly processed from natural materials) or synthetic. Dyes and colorants include synthetic dyes such as Liquitint® Yellow or Blue or natural plant dyes or pigments, such as a natural yellow, orange, red, and/or brown pigment, such as carotenoids, including, for example, beta-carotene and lycopene.

Water

When the composition is an aqueous composition, water can be, along with the solvent, a predominant ingredient. The water should be present at a level of less than 99.9%, more preferably less than about 99%, and most preferably, less than about 98%. Deionized water is preferred. Where the cleaning composition is concentrated, the water may be present in the composition at a concentration of less than about 85 wt.%.

Cleaning Substrate

The cleaning composition may be part of a cleaning substrate. A wide variety of materials can be used as the cleaning substrate. The substrate should have sufficient wet strength, abrasivity, loft and porosity. Examples of suitable substrates include, nonwoven substrates, wovens substrates, hydroentangled substrates, foams and sponges and similar materials which can be used alone or attached to a cleaning implement, such as a floor mop, handle, or a hand held cleaning tool, such as a toilet cleaning device. The terms "nonwoven" or "nonwoven web" means a web having a structure of individual fibers or threads which are interlaid, but not in an identifiable manner as in a knitted web. Nonwoven webs have been formed from many processes, such as, for example, melt-blowing processes, spunbonding processes, and bonded carded web processes.

EXAMPLES

Bioluminescence

Bioluminescence is a phenomenon where living organisms produce visible light (peak at 490 nm) by a biochemical reaction. The production of light is directly dependent on metabolic activity and viability of the organisms. Dead cells produce no light. As bioluminescence is widely used as an indicator for cell viability, the measurement of bioluminescence is a simple, fast and a reliable method for the detection of antibacterial effects of biocidal substances.

Biocide Efficacy Testing Using Bioluminescence

The biocidal properties of formulations were tested using bioluminescent (light emitting) reporter strains of Gram positive (G+) and Gram negative (G−) microorganisms and an optical imaging system equipped with a highly sensitive CCD camera capable of capturing photon emission, quantitatively in real time (Xenogen, Alameda, Calif.). Briefly, test disinfectant formulas were mixed at various concentrations with a standardized inoculum of reporter strains ($1 \times 10^8$ CFU/ml) in 96-well microtiter plates. Immediately after mixing, total photon emissions was quantified using the Living Image software package (Xenogen Corp) with measurements taking every 5 sec for a given experimental time window. The kinetics of biocidal action for each formula was monitored over time as a function of light emission.

Quantifying Biocide Efficacy

The Normalized Log Light Reduction (NLLR) at time T was calculated by taking the difference between the logarithm of the intensity of the emitted light of the positive control (inoculum untreated by disinfecting formulation) and the logarithm of the intensity of the emitted light from a treated sample (inoculum treated with disinfecting formulation) the formula, and dividing that by the difference between the logarithm of the intensity of the emitted light of the positive control and the logarithm of the emitted light from the negative control (well contains only sterile growth medium treated in the same way as a treated inoculum) at time T. Increasing NLLR values indicate increasing biocide efficacy. Slightly negative NLLR values indicate microbial growth instead of death as a result of treatment of an incolulum with a given formulation.

$$NLLR = (\log I_{positive\ control} - \log I_{treated\ sample}) / (\log I_{positive\ control} - \log I_{negative\ control})$$

Examples 1-2

In this example, a commercial solution of silver dihydrogen citrate (SDC) was diluted with deionized water to a concentration of 1.25% as is. This dilution delivers 30 parts per million of silver as silver dihydrogen citrate, and a significant excess of citric acid, ie. 0.22%. Thus, the diluted composition has a very low pH for stabilization of the soluble silver, as taught by Arata. The composition exhibits significant biocidal activity. However, adjustment of the same composition to pH 6.0 with caustic alone causes a severe reduction in the biocidal efficacy.

| | Sample Composition | | | NLLR at 25 min | |
|---|---|---|---|---|---|
| Example # | Ingredients | wt % | pH | Gram+ | Gram− |
| 1 | SDC | 1.25 | 2.2 | 0.89 | 0.95 |
| | DI water | balance | | | |
| 2 | SDC | 1.25 | 6.0 | 0.060 | 0.064 |
| | NaOH | to set pH | | | |
| | DI water | balance | | | |

Examples 3-4

In this example, sufficient MEA (monoethanolamine) was added to a dilution of commercially available SDC to form complexes with the silver ions and completely neutralize the excess citric acid delivered by the original SDC solution, resulting in a pH well above 6.0. The silver-MEA complexes exhibited significant antimicrobial efficacy. In the control experiment, the same amount of MEA and citric acid were combined to reach the same pH, but no silver was present. The control solution showed a lack of significant antimicrobial activity, indicating that the silver-MEA complexes were primarily responsible for the antimicrobial activity, not the MEA or citric acid (citrate ions) alone.

| Example # | Sample Composition Ingredients | wt % | pH | NLLR at 25 min Gram+ | Gram− |
|---|---|---|---|---|---|
| 3 | MEA | 0.69 | 9.5 | −0.1 | 0.12 |
|   | Citric acid | 0.22 | | | |
|   | DI water | balance | | | |
| 4 | SDC | 1.25 | 9.5 | 0.82 | 0.91 |
|   | MEA | 0.69 | | | |
|   | DI water | balance | | | |

Examples 5-7

These examples show that SDC can be used as a source of silver ions that are then complexed with MEA, and exhibit antimicrobial activity in formulations containing various surfactants, Ammonyx LO amine oxide and MES MC-48 sodium methyl α-sulfomethyl ester and the disodium α-sulfo fatty acid salt, at pH values above about 6.0. The formulations are useful as ready to use hard surface cleaners or disinfectants.

| Example # | Sample Composition Ingredients | wt % | pH | NLLR at 45 min Gram+ | Gram− |
|---|---|---|---|---|---|
| 5 | SDC | 1.25 | 9.5 | 0.86 | 0.83 |
|   | MEA | 0.69 | | | |
|   | Ammonyx LO | 2.0 | | | |
|   | DI water | balance | | | |
| 6 | SDC | 1.25 | 6.04 | 0.82 | 0.89 |
|   | MEA | 0.63 | | | |
|   | LAS | 1.91 | | | |
|   | DI water | balance | | | |
| 7 | SDC | 1.25 | 9.15 | 0.89 | 0.88 |
|   | MEA | 0.32 | | | |
|   | MES MC-48 | 0.33 | | | |
|   | DI water | balance | | | |

Examples 8-10

The following examples show that mono sodium glutamate (MSG), an amino acid salt, can be used as a chelant for silver ions delivered from SDC in formulations containing a variety of surfactants, Glucopon 225DK alkylpolyglucoside, SLS sodium lauryl sulfate and SAS sodium secondary alkyl sulfonate, at pH values much greater than 6.0. The antimicrobial activity of these formulations, which again contained 30 ppm silver ions, was checked at relatively short times, corresponding to the use of the formulations as disinfecting surface treatments or cleaners. These stable clear solutions exhibited rapid antimicrobial activity, indicating the soluble silver-MSG complexes were highly active.

| Example # | Sample Composition Ingredients | wt % | pH | NLLR at 3 min Gram− |
|---|---|---|---|---|
| 8 | SDC | 1.25 | 9.5 | 0.85 |
|   | MSG | 0.97 | | |
|   | Glucopon 225DK | 1.14 | | |
|   | NaOH | to set pH | | |
|   | DI water | balance | | |
| 9 | SDC | 1.25 | 9.5 | 0.45 |
|   | MSG | 0.95 | | |
|   | SLS | 2.05 | | |
|   | NaOH | to set pH | | |
|   | DI water | balance | | |
| 10 | SDC | 1.25 | 9.15 | 0.49 |
|   | MSG | 0.95 | | |
|   | SAS | 2.02 | | |
|   | NaOH | to set pH | | |
|   | DI water | balance | | |

Example 11-13

The following examples show that soluble silver ions, delivered from SDC, when present in formulations containing both MEA as a complexing agent and MSG as a chelant, exhibit antimicrobial activity even at relatively short times. The stable, clear formulations have pH values significantly greater pH 6, even greater than pH 9 or pH 10. These highly alkaline formulations exhibit good and rapid grease cutting performance, and are very useful as disinfecting hard surface cleaners.

| Example # | Sample Composition Ingredients | wt % | pH | NLLR at 3 min Gram− |
|---|---|---|---|---|
| 11 | SDC | 1.25 | 10.86 | 1.0 |
|   | MSG | 0.78 | | |
|   | MEA | 0.17 | | |
|   | Ammonyx LO | 1.97 | | |
|   | NaOH | to set pH | | |
|   | DI water | balance | | |
| 12 | SDC | 1.25 | 9.49 | 0.35 |
|   | MSG | 0.63 | | |
|   | MEA | 0.12 | | |
|   | SAS | 2.26 | | |
|   | NaOH | to set pH | | |
|   | DI water | balance | | |
| 13 | SDC | 1.25 | 9.55 | 0.46 |
|   | MSG | 0.81 | | |
|   | MEA | 0.15 | | |
|   | SAS | 2.07 | | |
|   | NaOH | to set pH | | |
|   | DI water | balance | | |

Example 14

This composition shows that soluble silver ions provided by SDC, can be stabilized at pH values greater than 6.0 when a chelant such as a salt of EDTA, ethylenediamine tetraacetic acid, is present in the formulation. A significant amount of a surfactant can be present, yielding a stable, clear composition that is useful as a disinfecting treatment or cleaner.

| Example | Composition | wt % | pH | NLLR at 30 min Gram+ | Gram− |
|---|---|---|---|---|---|
| 14 | SDC | 1.25 | 7.7 | 0.97 | 1.0 |
|  | Na2EDTA | 0.44 |  |  |  |
|  | SLS | 2.11 |  |  |  |
|  | NaOH | to set pH |  |  |  |
|  | DI water | balance |  |  |  |

Example 15-17

Example 15 serves as a control for Examples 16 and 17. A citric acid level of about 0.24% corresponds to the amount of excess citric acid provided by the commercial SDC used as a source of soluble silver ions, when the commercial SDC is diluted to 1.25%, yielding a silver ion concentration of 30 ppm. The combination of the citric acid and the chelant EDTA, adjusted to pH 9.2, shows no antimicrobial efficacy. In fact, the slightly negative NLLR values indicate slight growth in the inocula of both organisms treated with the composition of Example 15. Example 16, which contains soluble silver ions at 30 ppm, delivered by dilution of the SDC, exhibits very good antimicrobial efficacy when the chelant EDTA is present to provide stability at pH values greater than 6, and even greater than pH 9. Example 17 shows that good antimicrobial activity of soluble silver ions in the presence of the chelant EDTA is maintained even in tap water containing other ions, such as calcium and magnesium ions, that are known to interact with EDTA salts at pH values greater than 6.0. Thus, the use of EDTA can enable formulations designed to be added to tap water or formulations which can be diluted with tap water prior to use.

| Example # | Sample Composition Ingredients | wt % | pH | NLLR at 30 min Gram+ | Gram− |
|---|---|---|---|---|---|
| 15 | Citric acid | 0.24 | 9.2 | −0.16 | −0.09 |
|  | EDTA | 0.49 |  |  |  |
|  | NaOH | to set pH |  |  |  |
|  | DI water | balance |  |  |  |
| 16 | SDC | 1.25 | 9.2 | 0.71 | 0.89 |
|  | EDTA | 0.44 |  |  |  |
|  | NaOH | to set pH |  |  |  |
|  | DI water | balance |  |  |  |
| 17 | SDC | 1.25 | 9.5 | 0.67 | 0.78 |
|  | EDTA | 0.44 |  |  |  |
|  | NaOH | to set pH |  |  |  |
|  | Tap water | to balance |  |  |  |

An important aspect of this invention is the stabilization against precipitation of soluble silver ions in water containing significant amounts of ions, such as halides, particularly chloride, especially at pH values greater than 6.0. Chloride ions are often present as contaminants in commercial surfactants that are often used in cleaning compositions, and thus complicate the delivery of soluble silver ions in disinfecting cleaner formulations.

The stability of soluble silver ions stabilized by the presence of the complexing agents and/or the chelants of the present invention to chloride ion concentration was checked via a titration method. Thus, silver nitrate was used as a source of soluble silver ions to prepare a stock solution with a silver ion concentration of 0.0277 moles/liter. Stock solutions of MEA and MSG were also prepared at concentrations of 0.59 moles/liter. Typically, a 1 ml aliquot of the silver nitrate stock was then combined with various volumes of the MEA or MSG stocks (typically between 0 and 5 ml) or combinations of MEA and MSG, and an appropriate amount of pure water (resistivity 18.0 mOhm, from Millipore water treatment system) to produce titration sample solutions of 10 ml total starting volumes. These solutions were then titrated manually with a stock solution of sodium chloride (0.1993 moles/liter) in pure water until the first appearance of a precipitate of silver chloride, which would yield a hazy solution, was detected via observation. The chloride concentration in the solution at the appearance of precipitate is reported as the "chloride tolerance" below. Although the initial silver ion concentration in all samples was constant, the addition of varying volumes of the sodium chloride titrant diluted the samples slightly, to different degrees, and thus the ending silver concentrations varied somewhat. Also, it should be noted that, in order to aid detection of the first precipitate of silver chloride, the initial silver ion concentration was 0.00277 moles/liter, or about 298 ppm, which is much higher than the concentration typically used in disinfecting formulations. Thus, the benefits of the addition of complexing agents and chelants would be expected to be even better at lower silver concentrations, consistent with the preceding examples. The pH of the solutions containing silver ions and the MEA, or MSG, or mixtures of MEA and MSG at the precipitation endpoint of the titrations varied somewhat, but was always above pH 8, in all cases. The preparation of the silver solutions and the titrations were done in a double-blind fashion, i.e, by different operators. Each sample composition was prepared in triplicate and titrated, and thus the values of the chloride tolerance shown in the table below are the average of three measurements.

As the results in the table below for Example 18 show, the presence of the complexing agent MEA or the chelant MSG provided significant increases in the chloride tolerance, compared to the control solution of silver nitrate, which had an immeasurably small chloride tolerance of one drop of the sodium chloride titrant. An estimate of the titrant volume used in the titration of the control solution of silver ions of 0.025 ml was used to calculate the chloride tolerance of the control solution.

The results in the table below show that MSG is somewhat more effective than MEA at stabilizing soluble silver ions toward chloride ions, thus providing a larger chloride tolerance. Surprisingly, however, some mixtures of MEA and MSG show a synergistically higher chloride tolerance than the individual components or a weighted average of the two. Thus, formulations employing combinations of a complexing agent and an amino acid as a chelant are particularly useful for enhancing the chloride tolerance of practical formulations.

Example 18

| Sample Composition at first appearance of Chloride precipitate | | | | | | |
|---|---|---|---|---|---|---|
| Comp. | Ag+ ion mole/L | Ag+ ion, parts per million, wt/wt | MEA/Ag+ mole ratio | MSG/Ag+ mole ratio | MEA mole/L | MSG mole/L | Chloride tolerance Cl⁻ mole/L |
| 1 | 0.00211 | 227 | 107.1 | 0 | 0.226 | 0 | 0.048 |
| 2 | 0.00179 | 193 | 85.4 | 21.2 | 0.153 | 0.038 | 0.070 |
| 3 | 0.00162 | 175 | 64.2 | 42.6 | 0.104 | 0.069 | 0.083 |
| 4 | 0.00164 | 177 | 42.7 | 64.0 | 0.070 | 0.105 | 0.081 |
| 5 | 0.00170 | 183 | 21.2 | 85.3 | 0.036 | 0.145 | 0.077 |
| 6 | 0.00166 | 179 | 0 | 106.6 | 0 | 0.177 | 0.079 |
| 7 | 0.00277 | 298 | 0 | 0 | 0 | 0 | <0.0005 |

Chemical Key—SDC=Tinosan SDC, Pure Biosciences, described as containing 2400 ppm silver as silver dihydrogen citrate, and 20 wt % citric acid, MEA=monoethanolamine, SLS=sodium lauryl sulfate, LAS=linear alkyl benzene sulfonate, NA$_2$EDTA=disodium salt of ethylene diamine tetraacetic acid, MSG=mono-sodium glutamate, SAS=secondary alkane sulfonate.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

We claim:

1. An aqueous cleaning composition comprising:
   a plurality of complexes, wherein each complex comprises a silver cation and monoethanolamine; and
   from about 0.1% to about 2% by weight of an amine oxide surfactant, wherein the amine oxide surfactant is selected from the group consisting of a C10-C18 alkyl dimethylamine oxide, a C10-18 acylamido alkyl dimethylamine oxide, and mixtures thereof; and
   wherein the pH of the aqueous cleaning composition is greater than or equal to 9 and less than or equal to 11.

2. The aqueous cleaning composition of claim 1 further comprising glutamic acid or a sodium salt thereof.

* * * * *